United States Patent [19]

Butler

[11] Patent Number: 5,120,220
[45] Date of Patent: Jun. 9, 1992

[54] RIGHT ANGLED DENTAL HAND PIECE

[75] Inventor: David L. Butler, Millbrae, Calif.

[73] Assignee: BioDental Technologies Corporation, Rancho Cordova, Calif.

[21] Appl. No.: 621,809

[22] Filed: Dec. 4, 1990

[51] Int. Cl.[5] ............................................. A61C 3/06
[52] U.S. Cl. .................................... 433/125; 433/126
[58] Field of Search ............... 433/125, 126, 128, 133, 433/114, 112

[56] References Cited

U.S. PATENT DOCUMENTS

| 263,814 | 9/1882 | Schmitz | 433/112 |
|---|---|---|---|
| 1,999,488 | 4/1935 | Swisher et al. | 433/128 |
| 2,025,779 | 12/1935 | Roelke | 433/128 |
| 2,300,828 | 11/1942 | Goldenberg | 32/59 |
| 2,315,016 | 3/1943 | Shotton | 32/26 |
| 2,328,270 | 8/1943 | Greenberg | 74/56 |
| 3,163,934 | 1/1965 | Wiseman | 32/27 |
| 3,229,369 | 1/1966 | Hoffmeister et al. | 32/27 |
| 3,727,313 | 4/1973 | Graham | 433/125 |
| 3,740,853 | 6/1973 | Brahler | 433/112 |
| 3,987,550 | 10/1976 | Danne et al. | 433/133 X |
| 4,053,983 | 10/1977 | Flatland | 433/133 |
| 4,182,041 | 1/1980 | Girard | 433/125 X |
| 4,266,933 | 5/1981 | Warden et al. | 433/125 X |
| 5,020,994 | 6/1991 | Huang | 433/125 X |
| 5,028,233 | 7/1991 | Witherby | 433/125 |
| 5,040,978 | 8/1991 | Falcon et al. | 433/114 X |

FOREIGN PATENT DOCUMENTS 646193 6/1937 Fed. Rep. of Germany ...... 433/128

Primary Examiner—John J. Wilson
Assistant Examiner—Nicholas D. Lucchesi
Attorney, Agent, or Firm—Bernhard Kreten

[57] ABSTRACT

A device which fits onto a dental hand piece providing a spinning polishing cup at an angle to a long axis of the hand piece. A dental practitioner may use the device to effectively clean and polish teeth and prosthodontic structures within a patient's mouth. The device is disposable for greater sanitation. The device rotates in a direction in conformity with other fittings for dental hand pieces. The device is designed for easy manufacture by snapping a long gear and a short gear into contact with each other within a housing. Low friction secure interfaces between the short gear, the long gear and the housing allow the device to operate effectively at high speeds.

16 Claims, 3 Drawing Sheets

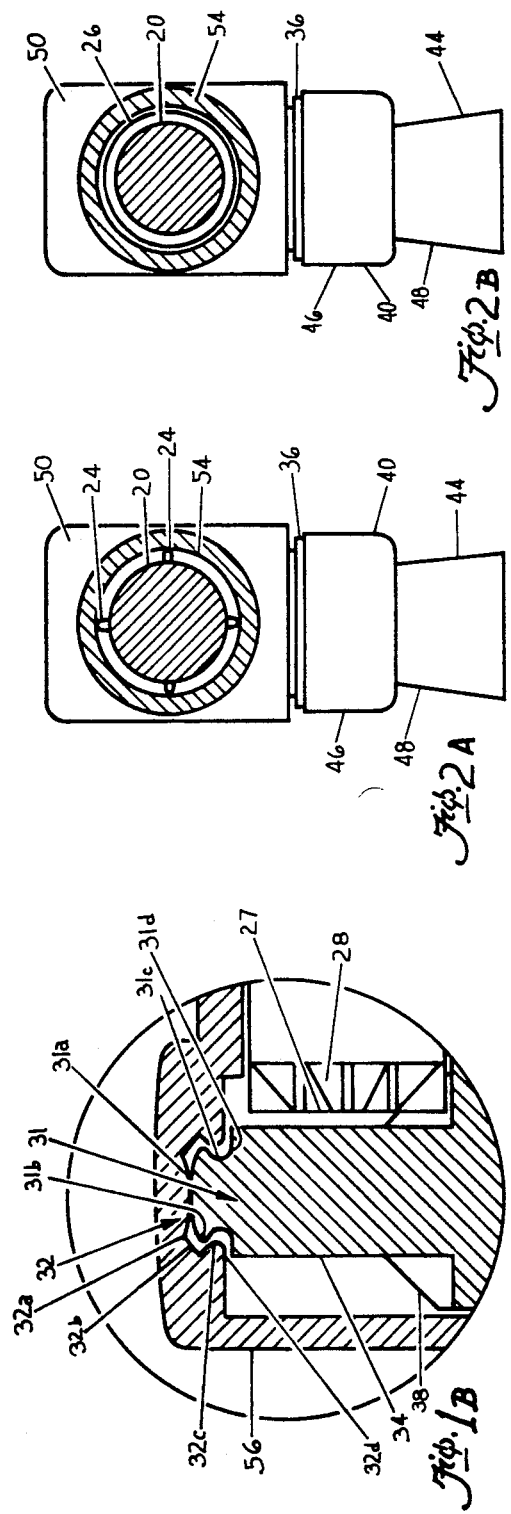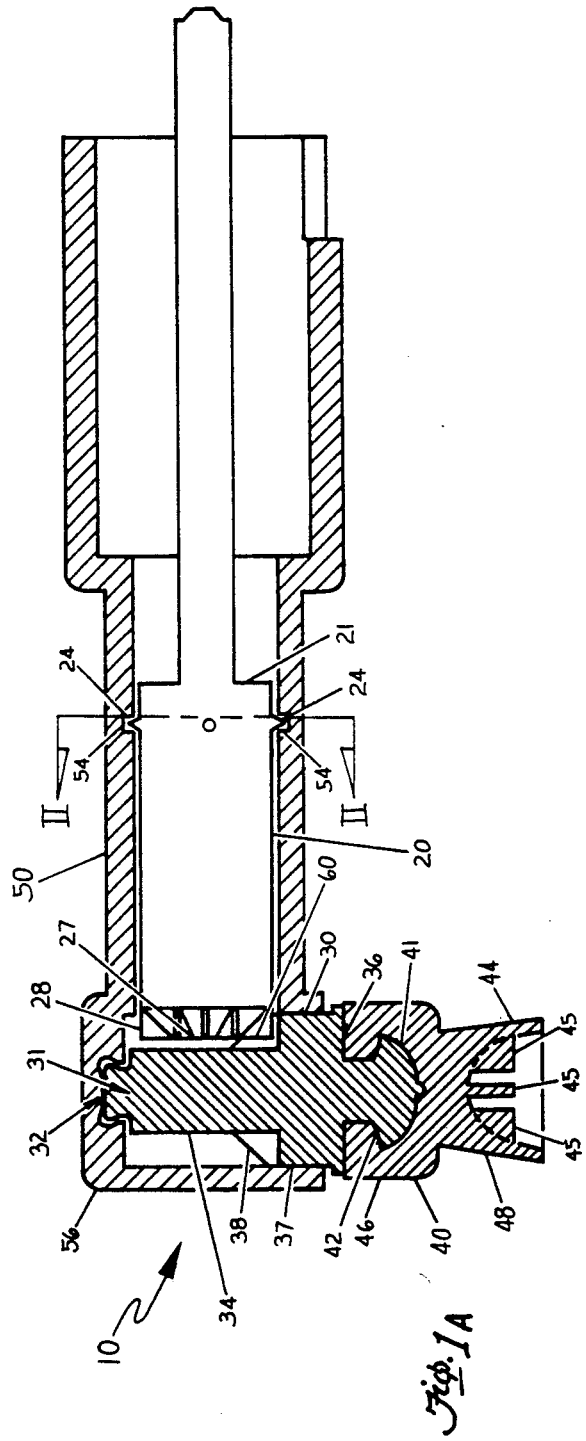

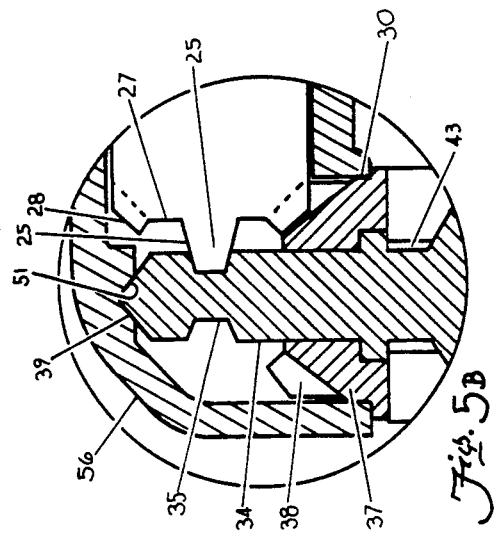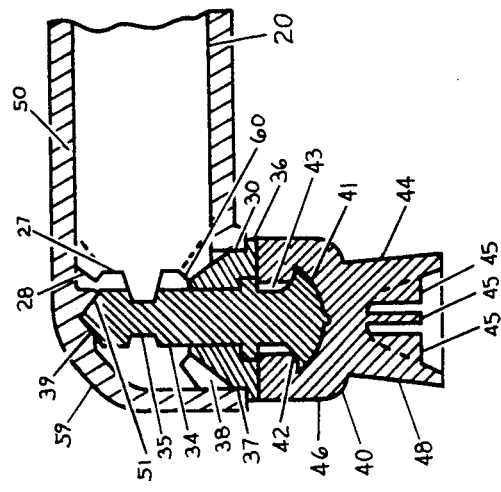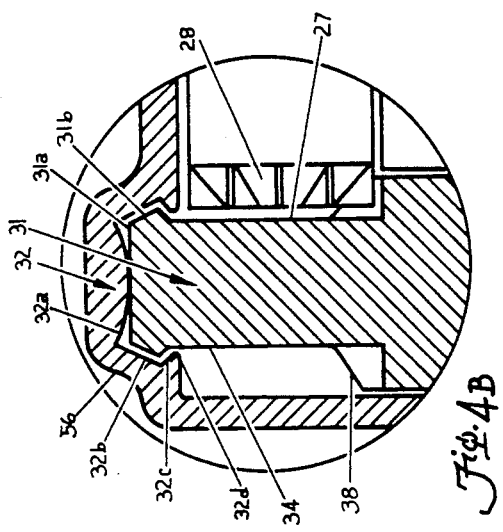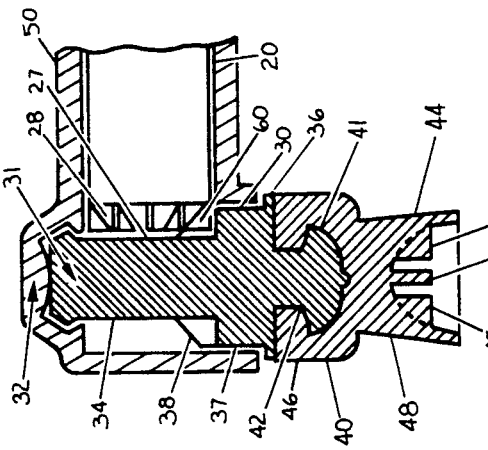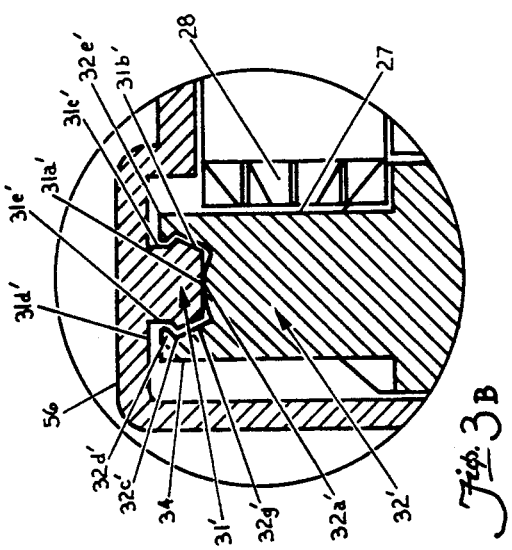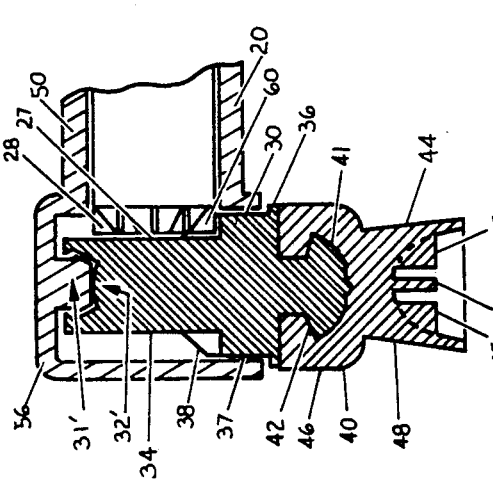

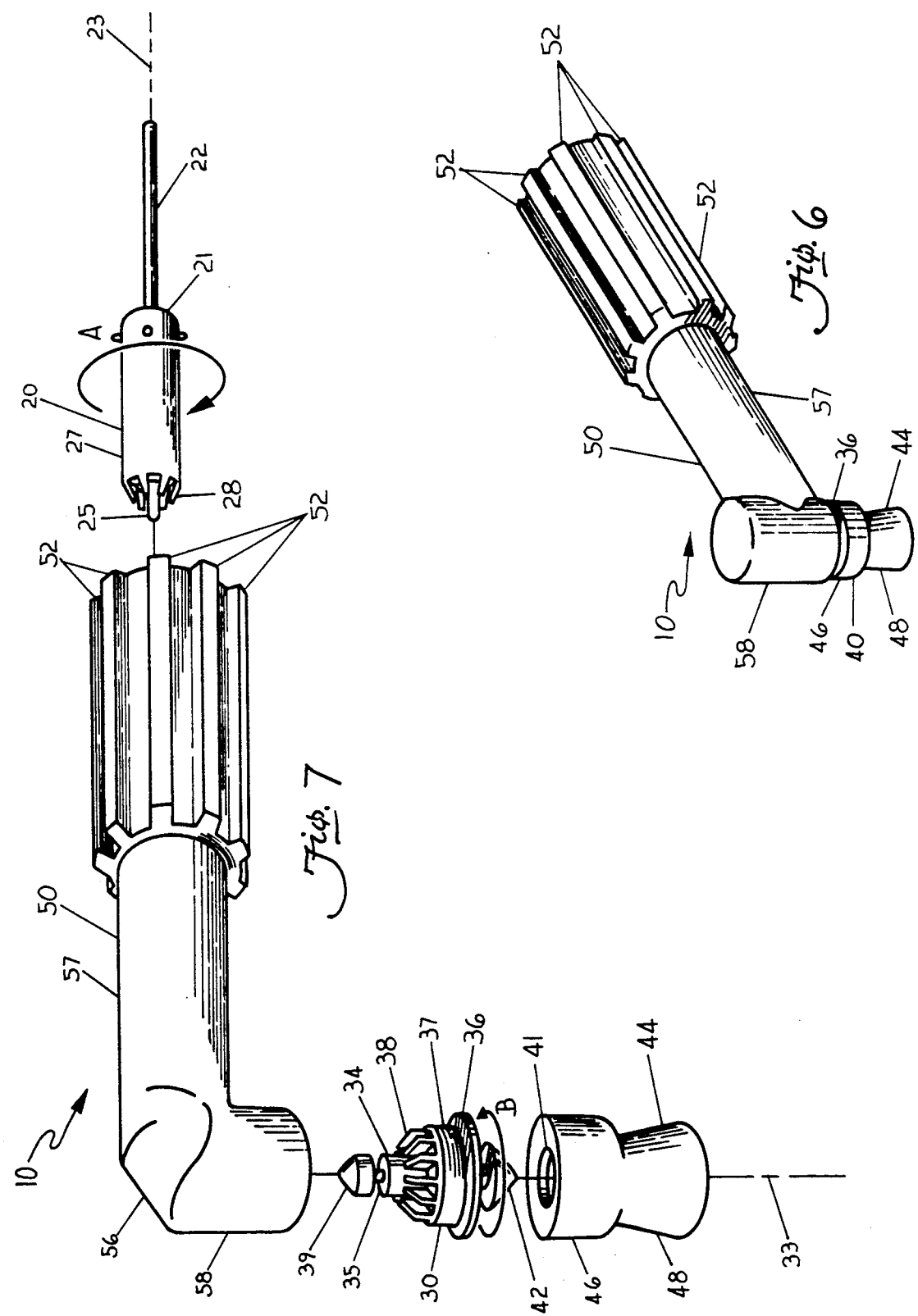

RIGHT ANGLED DENTAL HAND PIECE

FIELD OF THE INVENTION

This device relates to disposable prophylaxis fittings for dental hand pieces. More specifically, this device relates to fittings which have an angled tip and which incorporate gears into a housing which translate rotation first from an input, then to a gear in one axis of rotation, thence to a gear in another axis of rotation, and finally to a removable prophylaxis head attachment.

BACKGROUND OF THE INVENTION

When cleaning teeth and prosthodontic structures, dental practitioners often use commonly known disposable fittings for a power dental hand piece. These fittings have, on an output end, a cup capable of holding an abrasive polishing substance. The cup is rotated by the powered hand piece and through the disposable fittings. This allows the cup to apply the polishing substance and also perform the polishing function. After use on a patient, the fittings are disposed of.

One commonly known disposable fitting would benefit from improvement in a variety of ways. Most attachments to a dental hand piece rotate in a single direction of rotation. The commonly known disposable fitting, by design, always rotates counter to this common standard. This anomaly causes dental practitioners to compensate when using the apparatus, since rotational forces created by impacting the cup against the structures to be cleaned create "drift" which is always opposite from that anticipated by dental practitioners accustomed to ordinary hand piece attachments. To compensate, the practitioner can alter the drill rotation pneumatically but this requires subsequent reversion when another tool is used on the drill.

Furthermore, in assembling the commonly known disposable fitting, an integrally molded door is included which holds both of the gears of the fitting in close contact. This door being hinged only by a thin portion of plastic, requires critical engineering surveillance regarding cycle time and plastic recycling content because its elasticity is critical.

This invention solves the above and other problems in a new and useful way. It has an anticipated direction of rotation and has a means for holding the gears in place which is more easily manufactured and therefore provides even greater durability.

The following patents reflect the state of the art of which applicant is aware and are included herewith to discharge applicant's acknowledged duty to disclose relevant prior art. It is stipulated, however, that these references taken alone or in any conceivable combination do not teach the nexus of the instant invention as disclosed in greater detail hereinafter and as particularly claimed.

| INVENTOR | PATENT NO. | ISSUE DATE |
| --- | --- | --- |
| A. M. Goldenberg | 2,300,828 | November 3, 1942 |
| J. C. Shotton | 2,315,016 | March 30, 1943 |
| H. D. Greenberg | 2,328,270 | August 31, 1943 |
| A. D. Wiseman | 3,163,934 | January 5, 1965 |
| E. Hoffmeister et al. | 3,229,369 | January 18, 1966 |
| Graham | 3,727,313 | April 17, 1973 |

The Graham patent is of interest in that it teaches a disposable prophylaxis fitting for a dental hand piece comprised of a long gear and a short gear. However, the Graham patent teaches a gear interface on the exterior of the angle formed by the longitudinal axes of the two gears, rather than on the interior of that angle as does the applicant's instant device. Applicant's device thus spins in an opposite direction from the device of Graham when both devices receive an input of similar direction. Furthermore, applicant's device employs a means of long gear retention which improves on that taught by the Graham patent. Other structural distinctions and benefits result from these differences.

The Wiseman patent teaches a Dental prophylaxis right angle hand piece which is designed for removal and sterilization for re-use. The applicant's device is significantly different from Wiseman in that the applicant's device is disposable. This attribute allows for low cost manufacture and improved sanitation through only single use of the device.

The applicant's device is distinguishable from the Goldenberg patent in that the Goldenberg patent teaches an automatic feed of polishing compound to a tip of the hand piece. The Goldenberg patent also is designed to interface with a dental drill, not just a dental hand piece as does the applicant's. The remainder of the prior art cited above perform functions other than dental prophylaxis.

These other patents also are not designed to be disposable. Thus, the applicant's invention is distinguishable from these other prior art patents.

SUMMARY OF THE INVENTION

The invention of this application is a disposable prophylaxis angled attachment for a dental hand piece. Dental hand pieces commonly available have rotating output shafts designed to interface with a variety of attachments such as the device of this application. This device has a long gear and a short gear within a housing shell. The long gear interfaces on one end with the dental hand piece, and on the other end with the short gear. The rotational axis of the short gear is angled 90° from the rotational axis of the long gear.

An end of the short gear opposite the long gear has an attachment ball which can mate with a rubber polishing cup with a correlating attachment socket. When in place, this invention translates the rotational input of the hand piece into rotation of the polishing cup, allowing an operator to effectively clean teeth and prosthodontic structures within a patient's mouth.

This invention orients the two gears so that the direction of rotation will be that of most other hand piece attachments. The long gear of this invention is held in place against the short gear by a series of prominences which extend radially outwardly in the same plane, orthogonal to the rotational axis of the long gear. The housing of this attachment has a groove which holds these prominences allowing rotation but not linear translation. The short gear of this invention is held within the housing either by a ball and socket attachment or a modified ball and socket seat which cooperates with a groove on the short gear that captures a tongue on the long gear. This allows easy manufacture and assembly by snapping the short gear into place against the housing and also permits short gear rotation while restricting linear translation.

OBJECTS OF THE INVENTION

Accordingly, it is a primary object of this invention to provide a disposable prophylaxis attachment for a dental hand piece which rotates at an output end in a direction similar to other attachments for dental hand pieces.

Another object of this invention is to provide a means for retaining gears within the attachment housing of a disposable dental prophylaxis fitting for a hand piece which allows for ease of assembly, durability, and also effectively holds the gears together.

Another further object of this invention is to provide a device capable of low cost mass production allowing the device to be economical even when disposable.

Another further object of this invention is to provide a disposable cleaning apparatus, which avoids problems of sanitation through disposability.

Another further object of this invention is to provide a device which operates very safely even at extremely high speeds (as high as 10,000 RPM) while within a patient's mouth.

Another further object of this invention is to angle the polishing cup of the device to make the polishing cup come into contact more effectively with teeth and other prosthetic structures.

Viewed from a first vantage point it is an object of this invention to provide a disposable angled prophylactic fitting for a dental hand piece comprised of a L-shaped housing, a long gear within a long leg of the housing, a short gear within a short leg of the housing, and a means for holding the short gear within and by the L-shaped housing.

Viewed from another vantage point it is a further object of this invention to provide a disposable angled prophylatic fitting for a dental hand piece which includes a means for both rotatively supporting a gear within a long leg of a L-shaped housing and simultaneously precluding axial translation of the long gear.

Viewed from still another further vantage point it is an object of this invention to provide a disposable angled prophylactic fitting for a dental hand piece which connects a short gear and a long gear at a point which allows the short gear to rotate in a direction similar to other dental appliances.

It is still another further object of this invention to provide a method for causing a disposable dental angled prophylactic fitting to rotate at an output end in the same direction as other dental appliances.

BRIEF DESCRIPTION OF THE DRAWINGS FIGURES

FIG. 1A is a cross section of the apparatus.

FIG. 1B is a detail of that which is shown in FIG. 1A.

FIG. 2A is a cross section taken along line II—II of FIG. 1 showing a preferred means of long gear retention.

FIG. 2B is a cross section taken along line II—II of FIG. 1 showing an alternate means of long gear retention.

FIG. 3A is a cross section of an alternative design of the apparatus.

FIG. 3B is a detail of that which is shown in FIG. 3A.

FIG. 4A is a cross section of another alternative design of the apparatus.

FIG. 4B is a detail of what is shown in FIG. 4A.

FIG. 5A is a cross section of still another alternative design of the apparatus.

FIG. 5B is a detail of that which is shown in FIG. 5A.

FIG. 6 is an isometric view of the apparatus.

FIG. 7 is an exploded isometric view of the apparatus with the alternative design of FIG. 5.

DESCRIPTION OF THE PREFERRED EMBODIMENT

Referring now to the drawing figures where like numerals represent like parts throughout, numeral 10 is directed to a disposable angled prophylaxis fitting for a dental hand piece.

In essence, the prophylaxis fitting 10 shown in detail in FIG. 1A, is comprised of a housing 50 which contains a short gear 30 and a long gear 20 which contact each other at a gear contact region 60. The short gear 30 is a radially symmetrical construct having an upper end 34 rotationally attached to the housing 50, a lower end 37 removably attached to a polisher 40 and a plurality of short gear teeth 38 extending radially outwardly from the short gear 30 between the upper end 34 and the lower end 37. The long gear 20 is a radially symmetrical construct having an output end 27 adjacent to the short gear 30 with a plurality of long gear teeth 28 extending radially outwardly therefrom. The long gear teeth 28 and short gear teeth 38 interface together at the gear contact region 60. The long gear 20 has an input end 21 opposite the output end 27 which is fixedly attached to an input shaft 22 (FIG. 7). The input shaft 22 interfaces with a dental hand piece (not shown) which supplies rotation to the long gear 20, through the gear interface region 60, to the short gear 30 and on to the polisher 40, where a prophylaxis fitting 10 may be used to polish teeth or prosthodontic structures within a patient's mouth.

FIG. 1A shows a cross section of the prophylaxis fitting 10, revealing interior details. The housing 50, which is a hollow "L"-shaped construct, forms an exterior of the prophylaxis fitting 10. FIG. 6 shows that between a long leg 57 and a short leg 58 of the housing 50 a housing angle 56 is formed. Preferably, the housing angle is 90°. On the exterior of the long leg 57 of the housing 50 are a plurality of gripping ribs 52 extending longitudinally along a rear portion of the housing 50, as shown in FIG. 6 and FIG. 7. Within the housing 50 are two moving parts: the short gear 30 within the short leg 58 of the housing 50, and the long gear 20 within the long leg 57 fixedly attached to the input shaft 22.

The short gear 30 is held within the short leg 58 of the housing 50 by a matching short gear ball 31 and short gear socket 32 pair (FIG. 1A). In FIG. 1A the short gear ball 31 is fixedly attached to the upper end 34 of the short gear 30 and the short gear socket 32 is formed out of the housing 50 near the transition defining the housing angle 56.

As shown in detail in FIG. 1B, the ball 31 has a substantially planar top surface 31a and downwardly and first outwardly, then inwardly tapering side walls 31b interrupted by an arcuate transition therebetween which ultimately neck down to a cylindrical portion 31c which then translates radially outwardly to form a horizontal shelf 31d below the socket 32; thence communicating with the substantially cylindrical upper end 34.

Socket 32 includes a downwardly convex top surface 32a followed by a downwardly and outwardly extending chamfer wall 32b followed by a converging throat 32c parallel to sidewalls 31b. Thereafter the socket includes an annular portion 32d which circumscribes the ball 31. Annular portion 32d thereafter communicates with a horizontal top wall below which is the short leg 58 (FIG. 7) hollow interior of housing 50.

An alternative embodiment shown in FIG. 3A incorporates substantially the converse: the short gear ball 31' is fixedly attached to the housing 50 near the transition defining the housing angle 56, and locates the short gear socket 32' into the upper end 34 of the short gear 30.

Accordingly, the geometrical contours shown in detail in FIG. 3B are as follows: first, the ball 31' has a planar bottom surface 31a' and upwardly and first outwardly, then inwardly flared sidewalls 31b' which ultimately neck down to a converging throat 31c', followed by an annular portion 31e' which transitions to the top wall 31d' of the short leg hollow interior of housing 50 (FIG. 3A). Second, the socket 32' includes an upwardly convex bottom surface 32a' followed by an upwardly and outwardly flared chamfer wall 32g' which thereafter converges inwardly forming a throat 32c', then an annulus 32d' and finally a top wall 32e'.

The short gear ball 31' and short gear socket 32' are made of appropriate material and appropriately sized so that in manufacture the short gear 30 (FIG. 3A) may be snapped into the short leg 58 (FIG. 7) of the housing 50. The center points of the circular short gear ball 31' and short gear socket 32' are in line with a short gear rotational axis 33 shown in FIG. 7. In this configuration, the fitting 10 has distinct performance characteristics and exhibits a different level of ease of manufacture.

FIG. 4A shows another alternative embodiment of the means of attachment of the upper end 34 of the short gear 30 to the housing 50. The short gear ball 31 is fixedly attached to the short gear 30 and the short gear socket 32 is formed within the housing 50, similarly to the embodiment shown in FIG. 1A. However, the FIG. 4B detailed figure of this embodiment shows a ball 31 with side walls 31b which first diverge for only a short distance and then converge as they move away from the short gear 30 (FIG. 4A) until they reach a top surface 31a. This embodiment allows the short gear ball 31 to more easily snap into the short gear socket 32 because the top surface 31a is of shorter diameter than the diameter of an annular portion 32d.

The alternative embodiment of FIG. 4B does not include the horizontal shelf 31d shown in the embodiment of FIG. 1B. Instead, the FIG. 4B embodiment employs a ball 31 and socket 32 with diameters similar to the diameter of the upper end 34. The socket 32 of FIG. 4B remains substantially the same as the socket 32 of FIG. 1B, except a chamfer wall 32b extends farther before converging to the throat 32c in the FIG. 4B embodiment. This allows the embodiment of FIG. 4B to have less surface contact with the housing 50 than other embodiments when the prophylaxis fitting 10 is in use and forces are applied upwardly from the short gear 30 to the housing 50 through the short gear ball 31 and short gear socket 32. This embodiment also results in fewer curves in the exterior surface of the short gear 30 for applications where ease of manufacture is of primary importance.

FIG. 5A shows still another alternative embodiment of the means of contact of the upper end 34 of the short gear 30 to the housing 50. In this embodiment, retention is not the purpose, but rather the transfer of vertical loads from the short gear 30 to the housing 50 and maintenance of the alignment of the short gear 30. The embodiment of FIG. 5A does not snap. Rather, the corollary to the short gear socket 32 of FIG. 4A, formed in the housing 50, is merely a concave recess 51 in the housing 50 shown in detail in FIG. 5B. Similarly the corollary to the short gear ball 31 of FIG. 4, fixedly attached to the upper end 34 of the short gear 30, is now merely a convex prominence 39 of complemental shape to the concave recess 51. The joint action of the convex prominence 39 and the concave recess 51 is similar to that of a thrust bearing when the prophylaxis fitting 10 is in use, effectively transferring axial loads from the short gear 30 to the housing 50.

Once in place, the short gear 30 will be allowed to rotate freely about the short gear rotational axis 33, but otherwise the short gear 30 will be substantially restrained from movement, especially horizontal translation. In this configuration, the fitting 10 is characterized by a housing 50 with little detail on the interior surface, which makes it easier to manufacture at the tolerances necessary for high speed operation.

The polisher 40, shown in detail in FIGS. 1A, 3A, 4A and 5A, is connected to the lower end 37 of the short gear 30 and extends out of the short leg 58 of the housing 50. A polisher socket 41 is formed in one end 46 of the polisher 40 and conforms to a polisher ball 42 fixedly attached to the lower end 37 of the short gear 30. The polisher 40 has a polishing cup 44 integral with another end 48 of the polisher 40. Within the polishing cup 44 are a plurality of polishing ribs 45. The polishing cup 44 and polishing ribs 45 are designed to hold a chosen polishing compound and then apply the polishing compound when the prophylaxis fitting 10 is in use.

The polisher 40 is preferably constructed of a material such as soft rubber. This allows the polisher socket 41 to removable and frictionally attach to the polisher ball 42 of the short gear 30 without breakage. This allows the polisher cup 44 to conform to the surfaces of the teeth or prosthetic constructs to be cleaned when the prophylaxis fitting 10 is in use. FIG. 5A and FIG. 5B show an alternate embodiment of the polisher ball 42. A neck of the ball 42 is of lesser diameter than a constriction of the socket 41 creating a gap 43. When a polisher 40 with a modulus of elasticity of lesser value is used, the gap 43 decreases the amount of deflection the polisher socket 41 must undergo to fit over the polisher ball 42.

The short gear 30 has a short gear lip 36 extending radially outwardly relative to the short gear rotational axis 33 (FIG. 7) and at the lower end 37 of the short gear 30. The short gear lip 36 discourages contact between the polisher 40 and the housing 50, thus preserving a low friction interface between rotating and non-rotating parts.

Fixedly attached to the short gear 30 and extending radially outward relative to the short gear rotational axis 33 (FIG. 7) are the short gear teeth 38. Preferably, the short gear teeth 38 are wedge shaped constructs as shown in FIG. 5A, FIG. 5B and FIG. 7. The distance between adjacent short gear teeth 38 is somewhat greater than the thickness of the individual short gear teeth 38. In an alternative embodiment, the short gear teeth 38 may be substantially triangular in cross section as shown in FIG. 1A, FIG. 1B, FIG. 3A, FIG. 4A and FIG. 4B.

All of the short gear teeth 38 attach to the short gear 30 at a location below a rotational axis 23 (FIG. 7) of the long gear 20. This location guarantees that the rotation of the polisher 40 will be similar to that of other dental hand piece attachments.

When the prophylaxis fitting 10 is in use, both the short gear 30 and polisher 40 will rotate at high speeds, perhaps 10,000 RPM, about the short gear rotational axis 33. To avoid balancing problems the short gear 30 and polisher 40 are preferably substantially symmetrical radially.

The long gear 20 is a substantially cylindrical construct with a center of its diameter coextensive with the long gear rotational axis 23 (FIG. 7). The long gear 20 is preferably held in place by a plurality of prominences 24 which fit within a retaining groove 54. The retaining prominences 24 are fixedly attached to the long gear 20 and extend radially outwardly from the long gear 20. The retaining prominences 24 are all within a plane orthogonal to the long gear rotational axis 23. FIG. 2A shows in detail how the retaining prominences 24 extend from the long gear 20.

An alternative embodiment of FIG. 2A is shown in FIG. 2B. In place of retaining prominences 24 a retaining ring 26 is fixedly attached to the long gear 20 and extends radially outwardly from the long gear rotational axis 23 (FIG. 7). The retaining prominences 24 (or retaining ring 26) and the retaining groove 54 are made of appropriate material and appropriately sized in manufacture so that in assembly the long gear 20 may be snapped into the long leg 57 (FIG. 7) of the housing 50. Once in place the long gear 20 will be allowed to rotate freely about the long gear rotational axis 23, but otherwise the long gear 20 will be restrained, especially from axial movement.

The long gear 20 is fixedly attached at the input end 21 to the input shaft 22. The input shaft 22 is an elongate cylindrical construct with its longitudinal axis coincident with the long gear rotational axis 23 (see FIG. 7).

The long gear teeth 28 are fixedly attached to the long gear 20 at the output end 27 opposite from the input end 21. The long gear teeth 28 are preferably substantially wedge shaped constructs as shown in FIG. 5A, FIG. 5B and FIG. 7. In an alternative embodiment the long gear teeth 28 may be substantially triangular in cross section as shown in FIG. 1A, FIG. 1B, FIG. 3A, FIG. 3B, FIG. 4A and FIG. 4B.

The number of long gear teeth 28 is preferably identical to the number of short gear teeth 38, causing the amount of rotation of the long gear 20 to equal the amount of rotation of the short gear 30. The long gear teeth 28 are preferably the same size and shape as the short gear teeth 38, insuring that the gear contact region 60 can be maintained at an area which is large enough to support the loads encountered.

The housing 50 is sized along with the long gear 20 and short gear 30 such that when the long gear 20 and the short gear 30 are snapped into place within the housing 50 the long gear teeth 28 and the short gear teeth 38 interface at the gear contact region 60. In this configuration, rotation of the long gear 20 causes rotation of the short gear 30. When the long gear 20 is observed to rotate in a clockwise fashion as shown by arrow "A" in FIG. 7, as viewed along the long gear rotational axis 23, the short gear 30 will be observed entering the gear contact region 60 from the right and leaving the gear contact region 60 to the left as shown by arrow "B" in FIG. 7. This rotational orientation is similar to that of other dental hand piece fittings, allowing the dental practitioner to better utilize the prophylaxis fitting 10.

FIG. 5A, FIG. 5B and FIG. 7 show an alternative method of retention of the short gear 30 within the housing 50. A short gear groove 35 is formed radially on the short gear 30 between the upper end 34 and the lower end 37 of the short gear 30 and above the short gear teeth 38. A center of the short gear groove 35 is coextensive with the long gear rotational axis 23 shown in FIG. 7. Fixedly attached to the output end 27 of the long gear 20 is a long gear tongue 25. The long gear tongue 25 is substantially of the same diameter as the width of the short gear groove 35, such that when assembled the long gear tongue 25 resides within the short gear groove 35 restricting the short gear 30 from translating axially. In this embodiment, horizontal alignment is maintained by the interaction of the convex prominence 39 with the concave recess 51 (FIG. 5A) and vertical retainment is maintained by the interaction of the long gear tongue 25 with the short gear groove 35.

In use and operation, the prophylaxis fitting 10 connects to a dental hand piece allowing the input shaft 22 to couple with a rotational output of the dental hand piece 20. The input shaft 22 is thus rotated and causes the long gear 20 to rotate about the long gear rotational axis 23. The long gear then interfaces with the short gear 30 at the gear contact region 60 (FIG. 5A) causing rotation of the short gear 30 and the polisher 40 about the short gear rotational axis 33. A dental practitioner is then able to apply polish to teeth and other prosthodontic constructs, and is able to dispose of the prophylaxis fitting 10 when completed.

The prophylaxis fitting 10 is preferably manufactured from a lightweight low cost material. This allows the prophylaxis fitting 10 to be easily used, and inexpensively provided although disposable. Furthermore, the material used to manufacture the prophylaxis fitting 10 should resist failure under the loads experienced for at least a single use.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A disposable angled prophylactic fitting for a dental hand piece comprising, in combination:
   a unitary housing of substantially "L" shaped configuration having a long leg and a short leg defining said "L" shaped housing,
   a long gear residing within said long leg of said unitary housing,
   a short gear residing within said short leg of said unitary housing, and
   a means for attaching and rotatably supporting said short gear within and to said unitary housing,
   wherein said means for attaching and rotatably supporting said short gear is a groove circumscribing said short gear in a plane coextensive with a rotational axis of said long gear and perpendicular to a rotational axis of said short gear, and a circular tongue fixedly attached to said long gear at the center of an end of said long gear facing said short gear, said tongue being similar in diameter to the width of said groove, whereby said tongue of said long gear fits within said groove of said short gear restraining said short gear from linear movement while allowing rotation of said short gear and allowing rotation of said long gear.

2. The fitting of claim 1 wherein said long gear is supported in said long leg of said unitary housing by a complementally formed circumscribing recess and prominence allowing rotation but restricting linear motion of said long gear and holding said long gear and said short gear together.

3. The fitting of claim 2 wherein said prominence is broken into a plurality of discrete humps of equal height and spacing fixedly attached to said long gear and residing within said recess which is formed within said long leg of said unitary housing, whereby said long gear is retained with little friction.

4. The fitting of claim 2 wherein said prominence is broken into a plurality of discrete humps of equal height and spacing fixedly attached to said long leg of said unitary housing and residing within said recess which is formed within said long gear, whereby said long gear is retained with little friction.

5. The fitting of claim 4 wherein short gear teeth are fixedly attached to said short gear extending radially outwardly below said axis of rotation of said long gear and said short gear teeth contact long gear teeth at a point below said axis of rotation of said long gear, whereby said short gear rotates in a direction similar to other dental appliances.

6. A disposable angled prophylactic fitting for a dental hand piece comprising, in combination:
   a unitary housing of substantially "L" shaped configuration having a long leg and a short leg defining said "L" shaped housing,
   a long gear residing within said long leg of said unitary housing,
   a short gear residing within said short leg of said unitary housing, and
   a means for attaching and rotatably supporting said short gear within and to said unitary housing,
   wherein said means for attaching and rotatably supporting said short gear is a ball-and-socket type joint with a ball fixedly attached to said short gear and a socket fixedly attached to said unitary housing, whereby said ball-and-socket type joint holds said short gear in place within said short leg of said unitary housing and allows rotation of said short gear,
   wherein said ball is smaller in cross-section at an upper end than said socket at a lower end, whereby in manufacture said short gear may easily snap into said housing,
   wherein said socket is convex on an upper surface, thereby providing a smaller area of contact between said ball and said socket and hence a low friction interface between said short gear and said housing.

7. A disposable angled prophylactic fitting for a dental hand piece comprising, in combination:
   a unitary housing of substantially "L" shaped configuration having a long leg and a short leg defining said "L" shaped housing,
   a long gear residing within said long leg of said unitary housing,
   a short gear residing within said short leg of said unitary housing, and
   a means for attaching and rotatably supporting said short gear within and to said unitary housing,
   wherein said means for attaching and rotatably supporting said short gear is a ball-and-socket type joint with a ball fixedly attached to said unitary housing and a socket fixedly attached to said short gear, whereby said ball-and-socket type joint holds in place said short gear within said short leg of said unitary housing and allows rotation of said short gear,
   wherein said ball is smaller in cross-section at a lower end than said socket at an upper end, whereby in manufacture said short gear may easily snap onto said housing.

8. The fitting of claim 7 wherein said socket is convex on a lower surface, thereby providing a smaller area of contact between said ball and said socket and hence a low friction interface between said short gear and said housing.

9. A disposable dental angled prophylactic fitting for a hand piece comprising, in combination:
   a unitary housing of substantially "L" shaped configuration having one long leg and one short leg,
   a long gear adapted to reside within said long leg of said unitary housing,
   a short gear adapted to reside within said short leg of said unitary housing,
   a means for rotatably supporting said long gear within said unitary housing while constricting axial translation, and
   a means for attaching and rotatably supporting said short gear within and to said unitary housing; and
   wherein said means for attaching and rotatably supporting said short gear is a groove circumscribing said short gear in a plane coextensive with a rotational axis of said long gear and perpendicular to a rotational axis of said short gear, and a circular tongue fixedly attached to said long gear at the center of an end of said long gear facing said short gear, said tongue being similar in diameter to the width of said groove, whereby said tongue of said long gear fits within said groove of said short gear restraining said short gear from linear movement while allowing rotation of said short gear and allowing rotation of said long gear.

10. The fitting of claim 9 wherein said means for rotatably supporting said long gear is a plurality of prominences having a length extending radially outwardly from an outer surface of said long gear in a plane perpendicular to an axis of rotation of said long gear and a groove formed within an inner surface of said long leg of said unitary housing, said groove being as deep as said length of said prominences, whereby said prominences fit within said groove when said long gear is placed within said long leg of said unitary housing with teeth of said long gear in contact with teeth of said short gear effectively restraining said long gear from linear motion but allowing rotation of said long gear about said rotational axis of said long gear.

11. The fitting of claim 9 wherein said means for rotatably supporting said long gear is an annular prominence having a length extending radially outwardly from an outer surface of said long gear in a plane perpendicular to an axis of rotation of said long gear and a groove formed within an inner surface of said long leg of said unitary housing, said groove being as deep as said length of said prominence, whereby said prominence fits within said groove when said long gear is placed within said long leg of said unitary housing with teeth of said long gear in contact with teeth of said short gear effectively restricting said long gear from linear motion but allowing rotation of said long gear about said rotational axis of said long gear.

12. The fitting of claim 11 wherein said fitting includes a means for attaching and rotatably supporting said short gear within said unitary housing.

13. The fitting of claim 12 wherein said short gear interfaces with said long gear at a point below said rotational axis of said long gear, whereby said short gear rotates in a direction similar to other dental appliances.

14. A disposable dental angled prophylactic fitting as claimed in claim 9, further including:
- a means by which said long gear drives said short gear with a beveled gear disposed below said long gear;
- whereby when said long gear turns clockwise, said short gear turns through a contact point between said long gear and said short gear from right to left and when said long gear turns counter clockwise said short gear turns through said contact point from left to right.

15. A disposable angled prophylactic fitting for a dental hand piece, comprising, in combination:
- a unitary housing of substantially "L" shaped configuration having a long leg and a short leg defining said "L" shaped housing,
- a long gear residing within said long leg of said unitary housing,
- a short gear residing within said short leg of said unitary housing, and
- a means for attaching and rotatably supporting said short gear within and to said unitary housing; and
- wherein said means for attaching and rotatably supporting said short gear is a ball-and-socket type joint with a ball fixedly attached to said short gear and a socket fixedly attached to said unitary housing, whereby said ball-and-socket type joints holds said short gear in place within said short leg of said unitary housing and allows rotation of said short gear; and
- wherein said socket is convex on an upper surface, thereby providing a smaller area of contact between said ball and said socket and hence a low friction interface between said short gear and said housing.

16. A disposable angled prophylactic fitting for a dental hand piece, comprising, in combination:
- a unitary housing of substantially "L" shaped configuration having a long leg and a short leg defining said "L" shaped housing,
- a long gear residing within said long leg of said unitary housing,
- a short gear residing within said short leg of said unitary housing, and
- a means for attaching and rotatable supporting said short gear within and to said unitary housing; and
- wherein said means for attaching and rotatably supporting said short gear is a ball-and-socket type joint with a ball fixedly attached to said unitary housing and a socket fixedly attached to said short gear, whereby said ball-and-socket type joint holds in place said short gear within said short leg of said unitary housing and allows rotation of said short gear; and
- wherein said socket is convex on a lower surface, thereby providing a smaller area of contact between said ball and said socket and hence a low friction interface between said short gear and said housing.

* * * * *